United States Patent [19]

Taylor

[11] 4,105,678
[45] Aug. 8, 1978

[54] SYNTHESIS OF TETRAHYDROFURAN
[75] Inventor: Paul D. Taylor, Clinton, N.J.
[73] Assignee: Celanese Corporation, New York, N.Y.
[21] Appl. No.: 632,343
[22] Filed: Nov. 17, 1975
[51] Int. Cl.$^2$ ............................................. C07D 307/08
[52] U.S. Cl. ................................................ 260/346.11
[58] Field of Search ...................... 260/346.1 R, 346.11
[56] References Cited
U.S. PATENT DOCUMENTS

| | | | |
|---|---|---|---|
| T904,021 | 11/1972 | Copelin | 260/635 A |
| 2,251,835 | 8/1941 | Reppe et al. | 260/346.1 R |
| 2,888,492 | 5/1959 | Fischer et al. | 260/635 E |
| 3,929,915 | 12/1975 | Cumbo et al. | 260/346.1 |
| 3,954,877 | 5/1976 | Gipson | 260/604 HF |
| 4,044,059 | 8/1977 | Copelin | 260/346.11 |

Primary Examiner—Henry R. Jiles
Assistant Examiner—Bernard Dentz

[57] ABSTRACT

This invention provides a process for producing tetrahydrofuran by the reaction of 3-(5'-alkyl-1',3'-dioxane)-propionaldehyde and/or 3-(5'-alkyl-1',3'-dioxane)-propanol and/or 4-hydroxybutanal with hydrogen in an aqueous medium having a pH between about 0.1 and 5. Maintenance of the reaction medium within the specified acidic range of pH is an important feature of the invention process.

4 Claims, No Drawings

SYNTHESIS OF TETRAHYDROFURAN

BACKGROUND OF THE INVENTION

Tetrahydrofuran is an important organic material which finds application as a versatile solvent medium and as an intermediate for the production of resins and other commercial products such as butyrolactone and succinic acid.

Tetrahydrofuran can be produced by catalytic hydrogenation of maleic anhydride or furan, as is described in patent literature such as U.S. Pat. Nos. 2,772,293; 2,846,449; 3,021,342; and references cited therein.

It is well known that tetrahydrofuran can be produced by a series of reactions starting with the reaction of aqueous formaldehyde and acetylene in the presence of a cuprous acetylide complex to form butynediol. An alkaline material such as the carbonate, bicarbonate or hydroxide of an alkali or alkaline earth metal is commonly added to this reaction to control pH. This alkaline material generally reacts with the formic acid generated in this reaction to form the metal formate. The product of this reaction is then passed to a hydrogenation step where the butynediol is converted to butanediol.

The aqueous product stream from the hydrogenator is then concentrated to form a butanediol feed stream, typically containing, by weight, about 3 percent water, about 95-96 percent butanediol, and about 0.5-2 percent combined high boiling organic tars and alkali metal or alkaline earth metal salts. The butanediol is then converted to tetrahydrofuran using about 10 percent sulfuric acid. This reaction is carried out under temperature conditions which allow recovery of tetrahydrofuran and water overhead from the reactor. At equilibrium the reaction medium in the reactor typically contains about 50-60 percent unconverted butanediol, about 10 percent acid, about 10 percent water, and about 25 percent combined tars and salts. The build-up of tars and salts in the reactor is an undesirable characteristic of this type of process.

There is a need for new and improved commercial processes for the large volume production of tetrahydrofuran. The development of such processes is under active investigation.

Accordingly, it is an object of the present invention to provide a new and efficient method for producing tetrahydrofuran.

It is another object of the present invention to provide a method for converting 3-(5'-alkyl-1',3'-dioxane)-propionaldehyde and/or 3-(5'-alkyl-1',3'-dioxane)-propanol and/or 4-hydroxybutanal into tetrahydrofuran in high yield.

It is a further object of the present invention to provide a procedure for hydrogenating 3-(5'-methyl-1',3'-dioxane)propionaldehyde which can be integrated as an essential step in a commercially feasible process for converting acrolein into tetrahydrofuran.

Other objects and advantages shall become apparent from the accompanying description and examples.

DESCRIPTION OF THE INVENTION

One or more objects of the present invention are accomplished by the provision of a process which comprises contacting 3-(5'-alkyl-1',3'-dioxane)propionaldehyde with hydrogen in the presence of a hydrogenation catalyst and water in a reaction medium having a pH between about 0.1 and 5 to yield tetrahydrofuran and 2-alkyl-1,3-propanediol:

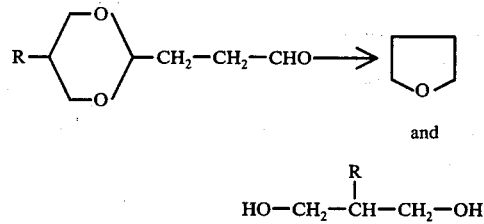

and

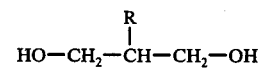

wherein R is an alkyl group containing between one and about five carbon atoms. In the present invention heterocyclic chemical structures, the propionaldehyde moiety is attached to the 2'-position of the 1',3'-dioxane structure, i.e., an "acetal" configuration.

Preparation of Starting Material

The 3-(5'-alkyl-1',3'-dioxane)propionaldehyde starting material can be provided in a high yield selectivity of at least 70 weight percent by a process which comprises reacting 2-vinyl-5-alkyl-1,3-dioxane with hydrogen and carbon monoxide in the presence of a hydroformylation catalyst at a temperature between about 25° and 200° C and a pressure between about 15 and 3000 psi.

Illustrative of a preferred embodiment of the hydroformylation reaction, 3-(5'-methyl-1',3'-dioxane)-propionaldehyde is produced in a yield of at least 80 weight percent by reacting 2-vinyl-5-methyl-1,3-dioxane with hydrogen and carbon monoxide in the presence of a metal-ligand complex hydroformylation catalyst at a temperature between 80° and 120° C and a pressure between about 75 and 150 psi. The relative amounts of hydrogen and carbon monoxide employed can vary in accordance with conventional hydroformylation processes, i.e., a molar ratio between 10:1 and 1:10. It has been observed that a high yield of 3-(5'-methyl-1',3'-dioxane)propionaldehyde is favored by increasing the relative ratio of hydrogen to carbon monoxide. Hence, to achieve the conversion of 2-vinyl-5-methyl-1,3-dioxane to 3-(5'-methyl-1',3'-dioxane)propionaldehyde in a yield of 85 weight percent and higher, a molar ratio of 1:1 to 5:1 of hydrogen to carbon monoxide is employed in the presence of a hydroformylation catalyst which is a complex of a Group VIII metal and a ligand containing phosphorus, arsenic and/or antimony elements.

The hydroformylation catalyst is generally employed in a quantity between about 0.001 and 5 weight percent, based on the weight of vinyl(1,3-dioxane) starting material, and preferably a weight percent quantity between about 0.01 and 1.0, exclusive of the weight of ligand if present.

The hydroformylation reaction may be carried out in a solvent, preferably one which is inert with respect to the products or starting materials, if desired. The solvent generally dissolves the catalyst, starting material and products. It is also possible to use the reaction products as the solvent. The latter is a commonly employed industrial expedient. A wide variety of organic solvents such as, for example, aromatics, aliphatics, esters, ethers, nitriles, alcohols, halogenated hydrocarbons, and the like, including benzene, cyclohexane, ethyl acetate, methyl alcohol, ethyl orthoformate, tetrahydrofuran, dioxane, isopropyl alcohol, aliphatic hydrocarbon cuts (saturated), chlorobenzene, methylene chloride, propionitrile, acetonitrile, trimethyl acetonitrile, and the like, and mixtures thereof may be employed.

For the operation of the hydroformylation reaction on a large scale, it is advantageous to exclude any solvent from the reaction medium. Excellent results can be achieved, for example, by employing a rhodium carbonyl catalyst component which is incorporated in a large excess of triphenyl phosphine. The said triphenyl phosphine can be included in the reaction medium in a quantity which is between 20 and 90 percent of the total weight of catalyst and vinyl(1,3-dioxane) reactant. Triphenyl phosphine at a temperature above about 80° C is highly fluid and performs as an excellent medium for the invention process.

If desired, the hydroformylation reaction can be conducted under conditions which are selected to yield an alcohol derivative rather than an aldehyde derivative for use as a starting material in the present invention process. Hence, what is contemplated is a process which comprises (1) reacting 2-vinyl-5-alkyl-1,3-dioxane with hydrogen and carbon monoxide in the presence of a metal-ligand complex hydroformylation catalyst at a temperature between about 80° and 120° C and a pressure between about 300 and 3000 psi to form 3-(5'-alkyl-1',3'-dioxane)-propionaldehyde, and (2) increasing the temperature to above about 150° C to convert said 3-(5'-alkyl-1',3'-dioxane)propionaldehyde to 3-(5'-alkyl-1',3'-dioxane)propanol.

A preferred class of catalysts for the two-step process for producing 3-(5'-alkyl-1',3'-dioxane)propanol derivatives are cobalt metal hydroformylation catalysts which are phosphine-modified. A suitable catalyst for such a process is a complex of cobalt metal, carbon monoxide and trialkyl phosphine (e.g., tributyl phosphine).

The temperature in the second step of the process is maintained in the range between about 150° and 225° C, and preferably at about 190° C. The pressure in the hydroformylation system is maintained in the range between about 300 and 3000 psi, and preferably between about 500 and 1000 psi.

2-vinyl-5-alkyl-1,3-dioxane when subjected to the selected hydroformylation conditions described hereinabove for the two-step process yields a mixture of 3-(5'-alkyl-1',3'-dioxane)propanol and 2-(5'-alkyl-1',3'-dioxane)propanol:

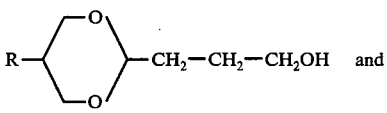

and

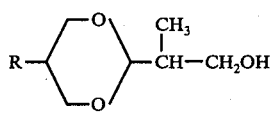

As it is apparent, the two-step hydroformylation process can be moderated to yield a mixture of aldehyde and alcohol derivatives as the product of the process. Also, the two-step process can be operated as a one-step process by maintaining the initial temperature above about 150° C rather than in the range of 80° to 120° C. At elevated temperatures the vinyldioxane starting material is more susceptible to hydrogenation to the corresponding ethyldioxane derivative.

As it is apparent from the following description and examples, the present invention hydrogenation process for producing tetrahydrofuran is generally applicable to dioxane starting material having the following structures:

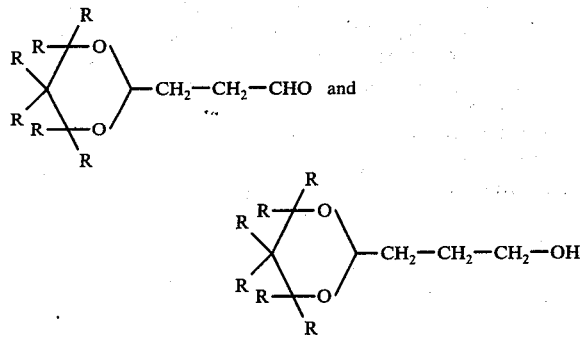

wherein R is hydrogen or an alkyl group containing between one and about five carbon atoms. A comprehensive description of the preparation of these dioxane starting materials is set forth in copending patent application Ser. No. 621,719, filed Oct. 14, 1975, which is incorporated herein by reference.

Hydrogenation Conditions

In accordance with a preferred embodiment of the present invention process for producing tetrahydrofuran, 3-(5'-alkyl-1',3'-dioxane)propionaldehyde and/or 3-(5'-alkyl-1',3'-dioxane)propanol and/or 4-hydroxybutanal is contacted with hydrogen in the presence of a hydrogenation catalyst and water in a reaction medium maintained at a pH in the range between about 0.2 and 3, and at a temperature between about 150° and 250° C and a pressure between about 15 and 1500 psi.

The hydrogenation catalysts suitable for use include metal catalysts such as platinum, palladium, silver, copper, vanadium, tungsten, cobalt, nickel, iron, ruthenium, rhodium, manganese, chromium, molybdenum, iridium, zirconium, and the like, and mixtures of the same and compounds and alloys thereof as described in prior art such as U.S. Pat. No. 2,840,617.

The hydrogenation catalyst can be employed in a finely divided form as a dispersion throughout the reaction medium. Or, the catalyst may be employed in the form of beads or pellets and the like, either in a pure state or supported upon or carried by an inert or catalytically active supporting or carrier material such as pumice, kieselguhr, diatomaceous earth, clay, alumina, charcoal, carbon, or the like. In the latter type supported hydrogenation catalysts, the reaction medium is contacted therewith by flowing the reaction medium over or through a bed of the catalyst, or by other contacting means known in the art.

The quantity of hydrogenation catalyst employed can vary over a broad weight range depending on the nature of the starting material and other processing conditions. For a batch type process, the quantity of hydrogenation catalyst normally can range between 1 and 30 weight percent, based on the weight of dioxane starting material, and preferably is in the range between about 1 and 10 weight percent.

The presence of water is required in the present invention process to achieve the hydrolysis-hydrogenation reaction mechanism which theoretically is involved. The quantity of water employed is at least the stoichiometric amount required to interact hydrolytically with the dioxane reactant. Preferably, the quantity of water in the reaction medium will vary between about one mole and 10 moles per mole of dioxane reactant, in a manner analogous to that described in U.S. Pat. No. 2,888,492.

The invention process preferably is conducted at a temperature in the range between about 180° and 225° C, and at a hydrogen pressure in the range between about 100 and 1000 psi.

It is an essential requirement of the present invention process that the pH of the reaction medium be maintained within the range between about 0.1 and 5, and preferably in the pH range between about 0.2 and 3. The conversion of 3-(5'-alkyl-1',3'-dioxane)propionaldehyde and/or 3-(5'-alkyl-1',3'-dioxane)propanol can be accomplished essentially quantitatively if the pH of the reaction medium is maintained in the preferred range, i.e., a pH range between about 0.2 and 3. The yield of tetrahydrofuran product diminishes as the pH of the reaction medium increases in basicity. If the pH of the reaction medium is in the range between about 5 and 7.5 then 1,4-butanediol is obtained as the main product instead of tetrahydrofuran. If the pH of the reaction medium is above 10, then the 3-(5'-alkyl-1',3'-dioxane)-propionaldehyde starting material undergoes diverse condensation-polymerization type reactions, and no tetrahydrofuran product is recoverable.

The pH of the reaction medium is conveniently maintained in the acidic range of pH by the addition of an appropriate quantity of a mineral acid such as sulfuric acid, or an organic acid such as acetic acid or p-toluenesulfonic acid. A polycarboxylic acid or an acidic ion-exchange resin may also be employed if desired.

At the conclusion of the present invention hydrogenation process, the tetrahydrofuran product can be recovered directly from the reaction product mixture by conventional procedures. The hydrogenation catalyst if dispersed as a fine powder, can be removed by filtration, centrifugation, or by other suitable means. For commercial scale operation, the process is preferably conducted as a continuous operation, and the catalyst, dioxane starting material, and 2-alkyl-1,3-propanediol by-product of the process are recycled in an appropriate manner.

UTILITY

The present invention process is a convenient and efficient method for producing tetrahydrofuran on an economically feasible commercial scale.

It is an important aspect of this invention that the hydrogenation process can be integrally incorporated as an essential step in a process for converting acrolein into tetrahydrofuran. For example, a new and efficient method for producing tetrahydrofuran comprises (1) condensing 2-methyl-1,3-propanediol with acrolein to form 2-vinyl-5-methyl-1,3-dioxane, (2) converting the 2-vinyl-5-methyl-1,3-dioxane in accordance with the hydroformylation method described hereinabove to a mixture of 2-(5'-methyl-1',3'-dioxane)propionaldehyde and 3-(5'-methyl-1',3'-dioxane)propionaldehyde, and (3) hydrogenating said mixture of propionaldehydes at a pH between about 0.1 and 5 in accordance with the present invention procedure to yield a mixture of tetrahydrofuran and 2-methyl-1,3-propanediol, and (4) separating the components of the product mixture, and recycling the 2-methyl-1,3-propanediol to the first step of the process.

The following examples are further illustrative of the present invention. The reactants and other specific ingredients are presented as being typical, and various modifications can be devised in view of the foregoing disclosure within the scope of the invention.

EXAMPLE I

Preparation Of 2-Vinyl-5-methyl-1,3-dioxane

Acrolein (59.5 grams) and 2-methyl-1,3-propanediol (83.8 grams) were added to benzene (100 grams) and p-toluenesulfonic acid (0.0596 gram) in a 500 ml flask equipped with a Dean-Stark trap, condenser, heating mantle and magnetic stirrer.

The mixture was heated at reflux for four hours with continuous removal of the water of reaction. The reaction mixture was cooled, neutralized with calcium oxide, filtered, and distilled to yield 66 grams of 2-vinyl-5-methyl-1,3-dioxane (65 percent yield).

When acrolein is condensed with 1,3-butanediol, the product obtained is 2-vinyl-4-methyl-1,3-dioxane.

EXAMPLE II

Preparation Of 3-(5'-methyl-1',3'-dioxane)propionaldehyde

A hydroformylation synthesis was conducted in a 300 ml magnetically stirred autoclave in the following manner.

Benzene (60 grams), triphenylphosphine (30 grams), hexa-rhodium hexadecyl-carbonyl [$Rh_6(CO)_{16}$, 0.20 grams] and 2-vinyl-5-methyl-1,3-dioxane (40 grams) were charged into the autoclave and with stirring heated at 90° C under a constant pressure of 90 psig carbon monoxide/hydrogen (1:1 mole ratio) for 105 minutes.

The reaction mixture was recovered and analyzed by gas chromatography. Analysis indicated that the reaction mixture contained 3-(5'-methyl-1',3'-dioxane)propionaldehyde (95 mole percent), 2-(5'-methyl-1',3'-dioxane)propionaldehyde (4 mole percent) and 2-ethyl-5-methyl-1,3-dioxane (1 mole percent). The overall yield to propionaldehydes was 98 percent.

If a cobalt metal-ligand complex hydroformylation catalyst is employed, an additional step of increasing the temperature to above about 150° and the pressure to above about 500 psi yields the corresponding propanol derivatives.

EXAMPLE III

Hydrogenation Of 3'-(5'-Methyl-1',3'-dioxane)propionaldehyde Under Essentially Neutral pH Conditions Acrolein and 2-methyl-1,3-propanediol were condensed to produce 2-vinyl-5-methyl-1,3-dioxane in accordance with the procedure of Example I.

2-vinyl-5-methyl-1,3-dioxane was hydroformylated in accordance with the procedure of Example II to yield a mixture of 3-(5'-methyl-1',3'-dioxane)propionaldehyde (95 mole percent) and 2-(5'-methyl-1',3'-dioxane)propionaldehyde (4 mole percent).

The said mixture of propionaldehydes (19.2 grams), water (29.6 grams) and Raney nickel (1.0 gram) were charged into a stirred autoclave. The reaction medium was heated up to 190° C over a 45 minute period at a constant hydrogen pressure of 300 psig. After the temperature was maintained at 190° C for an additional 15 minutes, the autoclave was cooled to room temperature and the reaction product mixture recovered. Gas chromatographic analysis indicated that the product mixture consisted essentially of 1,4-butanediol (43.8 mole percent) and 2-methyl-1,3-propanediol (56.2 mole percent).

During the hydrogenation reaction the pH of the reaction medium was maintained in the range between about 4 and 10 (i.e., an essentially neutral pH range).

EXAMPLE IV

Hydrogenation Of 3-(4'-Methyl-1',3'-dioxane)propionaldehyde Under Acidic Conditions Acrolein and 1,3-butanediol were condensed to produce 2-vinyl-4-methyl-1,3-dioxane in accordance with the procedure of Example I.

2-vinyl-4-methyl-1,3-dioxane was hydroformulated in accordance with the procedure of Example II to yield a mixture of 3-(4'-methyl-1',3'-dioxane)propionaldehyde (95 mole percent) and 2-(4'-methyl-1',3'-dioxane)propionaldehyde (4 mole percent).

The said mixture of propionaldehydes (5.0 grams), water (44.0 grams), 10% palladium on carbon powder (1.0 gram) and acetic acid (1.0 gram) were charged into a stirred autoclave. The pH of this mixture was 2.7. The reaction mixture was heated to 195° C over a 50 minute period at a hydrogen pressure of 350-435 psig. After the temperature was maintained at 195° C for an additional 15 minutes, the autoclave was cooled to room temperature and the reaction product recovered.

Gas chromatographic analysis indicated that the product mixture was essentially water, acetic acid, 1,3-butanediol and tetrahydrofuran. Essentially no 1,4-butanediol was detected. The pH of the mixture after the reaction was 2.9.

The same product mixture is produced if the organic starting material in the hydrogenation stage is a mixture of 3-(4'-methyl-1',3'-dioxane)propanol and 2-(4'-methyl-1',3'-dioxane)propanol.

The same product mixture is also produced if the organic starting material being hydrogenated is a mixture of 4-hydroxybutanal and 3-(4'-methyl-1',3'-dioxane)propionaldehyde and/or 3-(4'-methyl-1',3'-dioxane)propanol.

Under the same hydrogenation conditions, 4-hydroxybutanal converts in a mixture of tetrahydrofuran and 1,4-butanediol.

EXAMPLE V

Hydrogenation Of 3-(4'-Methyl-1',3'-dioxane)propionaldehyde Under Alkaline Conditions Acrolein and 1,3-butanediol were condensed to produce 2-vinyl-4-methyl-1,3-dioxane in accordance with the procedure of Example I.

2-vinyl-4-methyl-1,3-dioxane was hydroformylated in accordance with the procedure of Example II to yield a mixture of 3-(4'-methyl-1',3'-dioxane)propionaldehyde (95 mole %) and 2-(4'-methyl-1',3'-dioxane)propionaldehyde (4 mole %).

The said mixture of propionaldehydes (5.0 grams), water (45.0 grams), raney nickel (0.5 gram) and sodium hydroxide (0.2 gram) were charged into a stirred autoclave. The pH of this mixture was 12.18. The reaction mixture was heated to 200° C over a period of 50 minutes at a hydrogen pressure of 400-500 psig. After the temperature was maintained at 200° C for an additional 100 minutes, the autoclave was cooled to room temperature and the reaction product recovered.

Gas chromatographic analysis indicated that the product mixture was essentially water, about 30% of the theoretical 1,3-butanediol, and polymeric materials. Essentially no 1,4-butanediol was detected. The pH of the mixture after the reaction was 7.5.

EXAMPLE VI

Conversion Of Allyl Alcohol To 4-Hydroxybutanal

Allyl alcohol (10 grams), benzene (40 grams), triphenyl phosphine (30 grams) and hexarhodium hexadecyl carbonyl (0.05 grams) were sealed in a 300 ml "Magnadrive" autoclave. The vessel was pressured with carbon monoxide to 90 psig and depressurized twice then heated to 80° C. A mixture of carbon monoxide and hydrogen (1:1 mole ratio) was admitted to the vessel until the pressure reached 90 psig. Constant gas pressure was maintained on the reaction vessel by means of a pressure regulator attached to a one liter storage vessel also containing a mixture of carbon monoxide and hydrogen (1:1 mole ratio). Gas absorption ceased after 40 minutes. The reactor was cooled to room temperature and the liquid contents analyzed by gas chromatography. The allyl alcohol conversion was found to be 99% to 4-hydroxybutanal (87 wt%), 2-methyl-3-hydroxypropanal (12 wt%) and propanal (1 wt%).

EXAMPLE VII

Conversion Of 4-Hydroxybutanal To Tetrahydrofuran

The liquid contents from Example VI were extracted with two 25 ml portions of water. A gas chromatograph of the benzene/triphenyl phosphine/rhodium carbonyl showed only traces of aldehydes indicating quantitative extraction of the products by water. These aqueous extracts were mixed with acetic acid (5.1 grams) and hydrogenated with 5% palladium on carbon (2.0 grams) at 114° C for two hours under 1000 psig hydrogen pressure in a "Magnadrive" autoclave, then the temperature was increased to 166° C for one hour. Gas chromatographic analysis of the resulting reaction mixture indicated 100% conversion to a mixture of tetrahydrofuran (45 wt%), 2-methyl-1,3-propanediol (10 wt%), and 1,4-butanediol (45 wt%).

When the hydrogenation reaction was conducted at a temperature of 190° C, within a period of about one hour the 4-hydroxybutanal converted quantitatively into tetrahydrofuran.

What is claimed is:

1. A process which comprises contacting 3-(5'-alkyl-1',3'-dioxane)propionaldehyde with hydrogen in the presence of a hydrogenation catalyst at a temperature between about 180° C and 225° C and a pressure between about 100 and 1000 psi in an aqueous medium maintained at a pH between about 0.2 and 3 with a water-soluble acid to produce tetrahydrofuran, and recovering the said tetrahydrofuran from the reaction mixture.

2. A process which comprises contacting a mixture of 3-(5'-methyl-1',3'-dioxane)propionaldehyde and 2-(5'-methyl-1',3'-dioxane)propionaldehyde with hydrogen in the presence of a hydrogenation catalyst at a temperature between about 180° and 225° C and a pressure between about 100 and 1000 psi in an aqueous medium maintained at a pH between about 0.2 and 3 with a water-soluble acid to produce a product mixture of tetrahydrofuran and 2-methyl-1,3-propanediol, and recovering the tetrahydrofuran from the product mixture.

3. A process in accordance with claim 2 wherein the 3-(5'-methyl-1',3'-dioxane)propionaldehyde is at least about 80 weight percent of the starting mixture.

4. A process which comprises contacting a mixture of 3-(5'-methyl-1',3'-dioxane)propanol and 2-(5'-methyl-1',3'-dioxane)propanol with hydrogen in the presence of a hydrogenation catalyst at a temperature between about 180° and 225° C and a pressure between about 100 and 1000 psi in an aqueous medium maintained at a pH between about 0.2 and 3 with a water-soluble acid to produce a product mixture of tetrahydrofuran and 2-methyl-1,3-propanediol, and recovering the tetrahydrofuran from the product mixture.

* * * * *